United States Patent [19]
Kiser

[11] Patent Number: 5,727,568
[45] Date of Patent: Mar. 17, 1998

[54] MALE INCONTINENCE TREATMENT DEVICE

[76] Inventor: G. Craig Kiser, 10771 NW. Bretano La., McMinnville, Oreg. 97128

[21] Appl. No.: 742,458

[22] Filed: Nov. 1, 1996

[51] Int. Cl.$^6$ ................................................. A61F 5/48
[52] U.S. Cl. ........................... 128/885; 128/DIG. 25
[58] Field of Search ........................ 128/95.1, 96.1, 128/98.1, 100.1, 105.1, 842, 844, 885, 918, DIG. 25; 602/67, 68, 69; 600/29–31

[56] References Cited

U.S. PATENT DOCUMENTS

| | | |
|---|---|---|
| 2,602,444 | 7/1952 | Stanford . |
| 2,756,753 | 7/1956 | Means . |
| 3,066,667 | 12/1962 | Berry . |
| 3,147,754 | 9/1964 | Koessler .................... 128/885 |
| 3,155,096 | 11/1964 | Outwin ...................... 128/885 |
| 3,866,611 | 2/1975 | Baumrucker . |
| 4,139,006 | 2/1979 | Corey . |
| 4,206,752 | 6/1980 | Witton ........................ 600/39 |
| 4,880,016 | 11/1989 | Worth et al. . |
| 5,094,234 | 3/1992 | Searcy ........................ 602/68 |
| 5,184,629 | 2/1993 | Erickson et al. . |
| 5,439,007 | 8/1995 | Fischer . |

Primary Examiner—Michael A. Brown
Attorney, Agent, or Firm—Robert D. Varitz

[57] ABSTRACT

A male incontinence treatment device a flow-restricting device which is worn in a position such that the urethra is compressed between the device and the pubic bone of the wearer. A fixing mechanism for holding the flow-restricting device in place is provided, which fixing device may take the form of an undergarment.

16 Claims, 3 Drawing Sheets

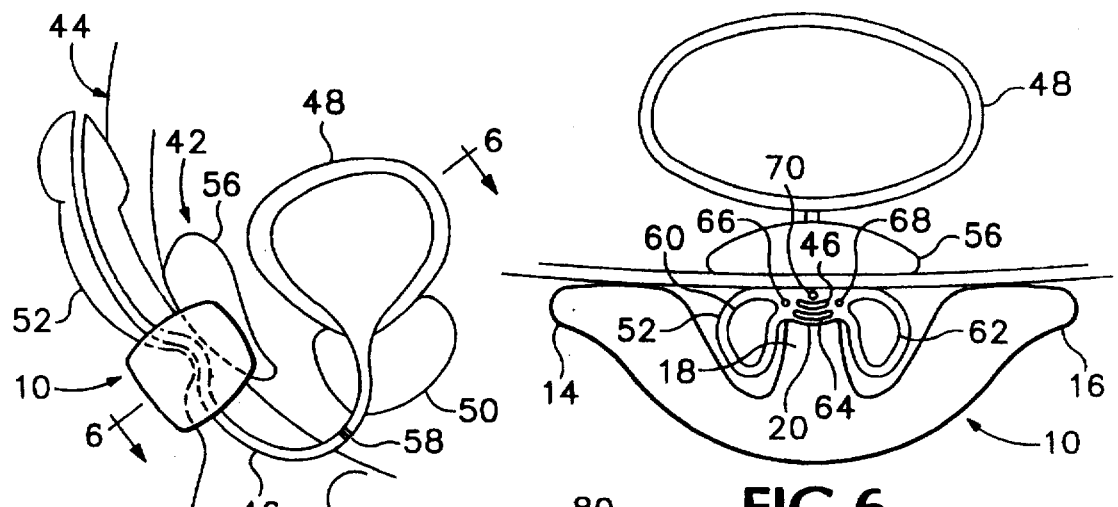
FIG.5
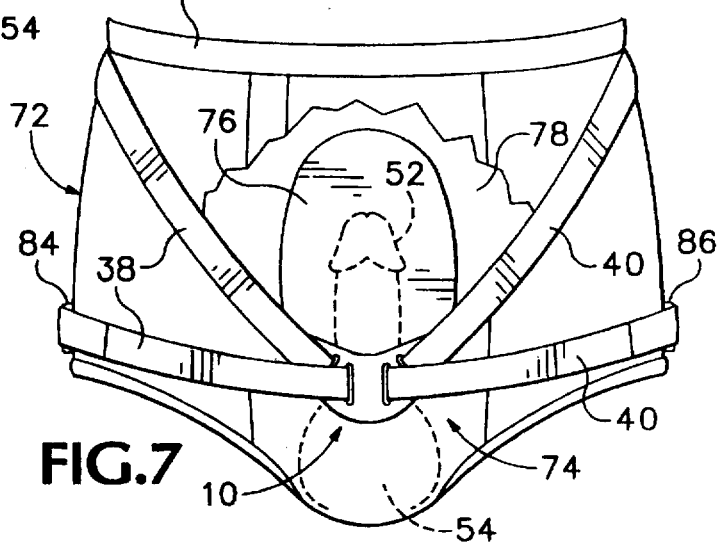
FIG.6
FIG.7
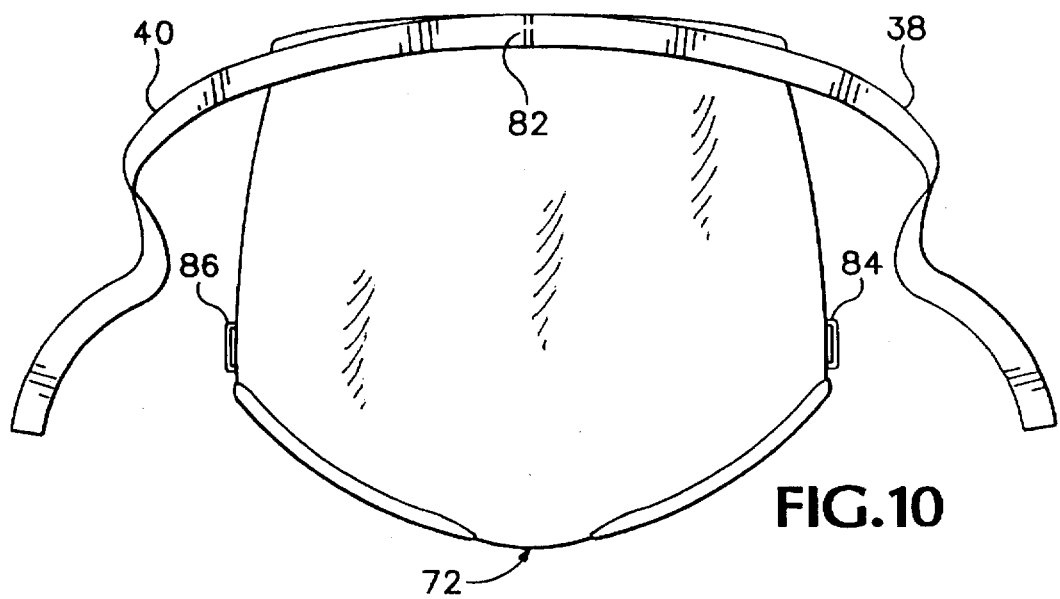
FIG.10

5,727,568

MALE INCONTINENCE TREATMENT DEVICE

FIELD OF THE INVENTION

The invention described herein relates to the treatment of the condition of male urinary incontinence, and specifically to a device which is used to compress the urethra to a closed position of exerting a compressing force on the urethra between the device and the pubic synthesis.

BACKGROUND OF THE INVENTION

Urinary incontinence, hereinafter referred to as incontinence, may have a number of causes, however, the failure of the sphincter muscles, specifically the internal and external urethral sphincters, in the urethra to close either partially or completely is the underlying cause of incontinence. Incontinence may be a natural occurrence, as a result of the weakening of the muscle, failure of the muscle to develop or a temporary nervous disorder, as might be caused by stress, or it might be the result, particularly in men, of prostrate surgery.

In any event, incontinence is an unsanitary and inconvenient condition, which may also be psychologically demoralizing and result in depression. A number of protocols have been used to control incontinence. Perhaps the most primitive sort of device is the provision of a condom-catheter external urinary collection device, which is worn by the incontinent individual, wherein a urine reservoir is strapped to the wearer's leg, and which has a catchment device in contract with the penis.

Another form of protocol is to simply wear an absorbent pad. This, however, causes significant problems for the wearer, not the least of which is the odor associated with the pad, and the requirement to frequently change the pad, which is capable or storing only a limited volume of urine.

In the case of male incontinence, a number of penile clamp devices are known, all of which have drawbacks. In most cases, the clamp encircles the penis and collapses not only the urethra, but exerts force on the two corpora cavernosa, the three main penile veins, and, in most cases, substantially the entire circumference of the skin about the penis. In an extreme case, the flow of blood in and out of the penis may be stopped, which will result in tissue necrosis. Such devices are generally bulky and structurally complicated, and may also result in a semi-permanent, involuntary erection.

Clamp devices which purport to contact only a portion of the penile surface while compressing the urethra are shown in U.S. Pat. No. 3,155,096 to Outwin, and U.S. Pat. No. 3,147,754, to Koessler. Devices which substantially encircle the entire penis are shown in U.S. Pat. No. 2,756,753, to Means, U.S. Pat. No. 3,866,611, to Baumrucker, U.S. Pat. No. 4,880,016 to Worth et al., and U.S. Pat. No. 5,184,629 to Erickson et al.

Another protocol for reducing male incontinence is shown in U.S. Pat. No. 3,066,667, to Berry, and involves a surgical procedure to insert a device into a pocket located between the bulbocavernosus muscle and the urethra, in a position adjacent to the urethra, and then training the individual to maintain the bulbocavernosus muscle in a tensed condition, thereby maintaining a closing pressure on the urethra by the surgically-implanted device.

It should be noted that none of the foregoing protocols provide for a 100% effective stoppage of urine flow in the case of an incontinent individual.

SUMMARY OF THE INVENTION

The male incontinence treatment device of the invention includes a flow-restricting device which is worn in a position such that the urethra is compressed between the device and the pubic bone of the wearer. A fixing mechanism for holding the flow-restricting device in place is provided, as is an undergarment which may be worn in conjunction with the device.

An object of the Invention is to provide a male incontinence treatment device which substantially closes the urethra without exerting a significant clamping force on the penile shaft.

Another object of the invention is to provide such a device which is substantially invisible under clothing.

A further object of the invention is to provide such a device which does not require the unfastening of clamps prior to urination.

Yet another object of the invention is to provide such a device which is inexpensive, biologically inert, hygienically safe, and easy to clean.

Another object of the invention is to provide such a device which does not result in restriction in penile blood supply.

These and other objects and advantages of the invention will become more fully appreciated as the description which follows is read in connection with the drawings.

BRIEF DESCRIPTION OF THE DRAWINGS

FIG. 5 is a medial sagittal section taken through the male urinary tract, depicting the flow-restricting device in a functional position.

FIG. 6 is a section taken generally along the line 6—6 of FIG. 5.

FIG. 7 is a front elevation of the device as affixed to an undergarment containing a fixing mechanism therefor.

FIG. 10 is a rear elevation of the undergarment of FIG. 9.

BEST MODE OF PRACTICING THE INVENTION

Figure 1:
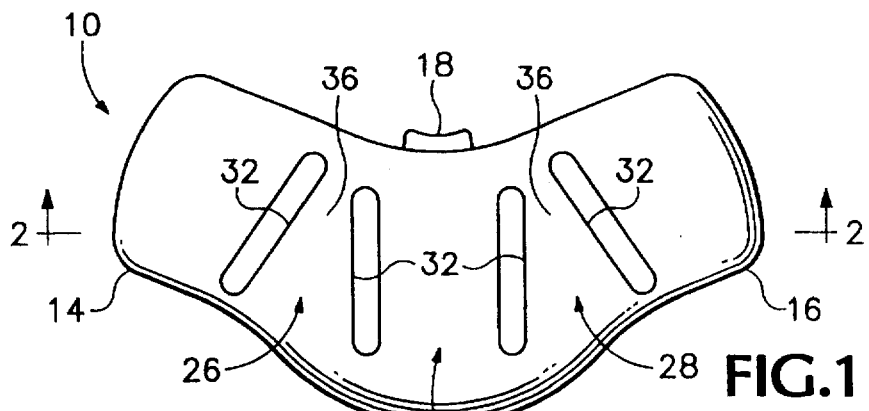
FIG. 1 is a front elevation of flow-restricting device of the invention.
Figure 2:
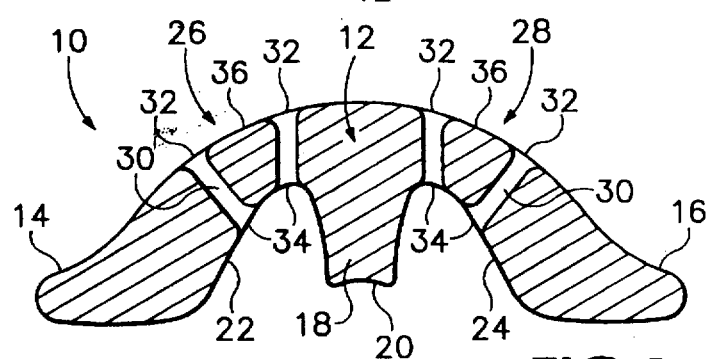
FIG. 2 is a bottom plan section of the flow-restricting device, taken generally along the line 2—2 of FIG. 1.
Figure 3:
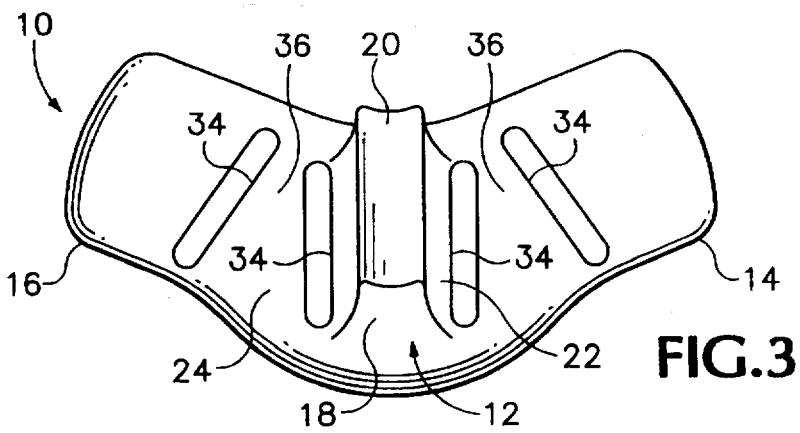
FIG. 3 is a rear view of the flow-restricting device.

Referring now to the drawings, and initially to FIGS. 1, 2 and 3, a flow-restricting device is depicted generally at 10. Device 10, in the preferred embodiment, is formed of a biologically-inert material, such as a plastic, silicone or suitable metal. Device 10 includes a central body portion 12 and a pair of laterally-extending wings 14, 16. Wings 14 and 16 extend rearwardly relative to a wearer, and provide lateral stabilization for device 10. The post 18 extends rearwardly from central body 12. Post 18 has a concave, urethra-bearing surface 20, located at the free end thereof. The region between wings 14 and 16 and post 18 comprise what is referred to herein as penis-cradling surfaces 22, 24, which are located on either side of post 18. Penis-cradling surfaces 22, 24 are concave structures, and extend along the rear surface of wings 14, 16, respectively, and then along the lateral sides of post 18, terminating at urethra-bearing surface 20.

Device 10 includes a fixing-mechanism receiver which is located on body 12, on either side thereof, and designated generally by reference numbers 26, 28. In a preferred embodiment, receivers 26 and 28 include a channel 30 which intersect the front and rear surfaces of the device at slots 32, 34, respectively, which slots are separated by a bridge 36.

Figure 4:
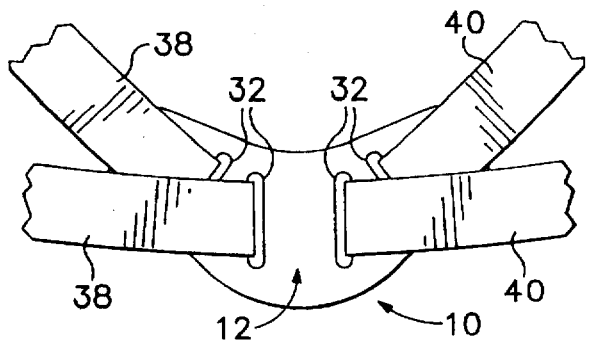
FIG. 4 is a front elevation of the device and a fixing mechanism therefor.
Figure 8:
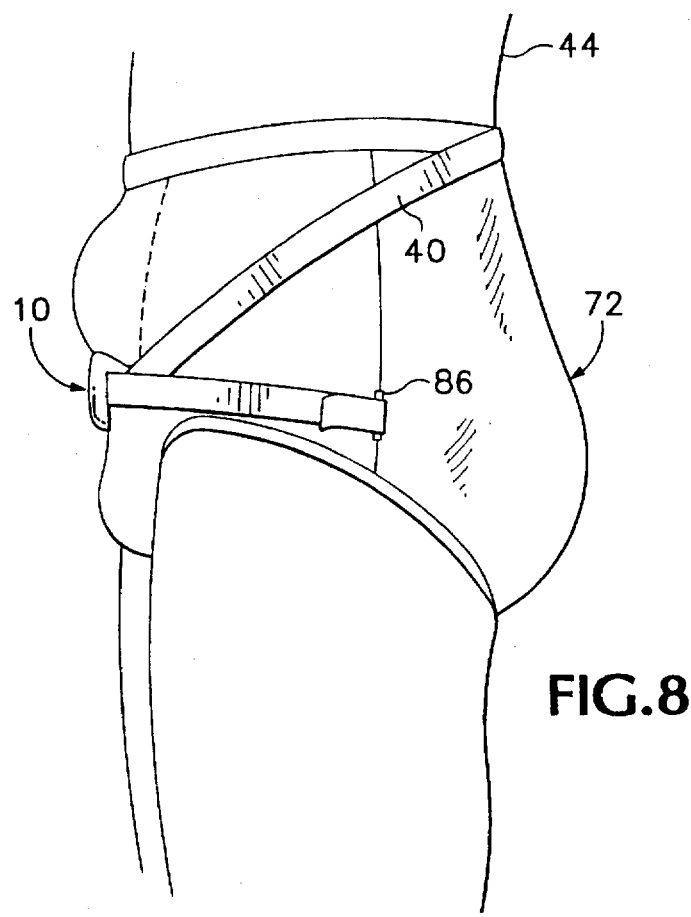
FIG. 8 is a side elevation of the device and undergarment of FIG. 7.
Figure 9:
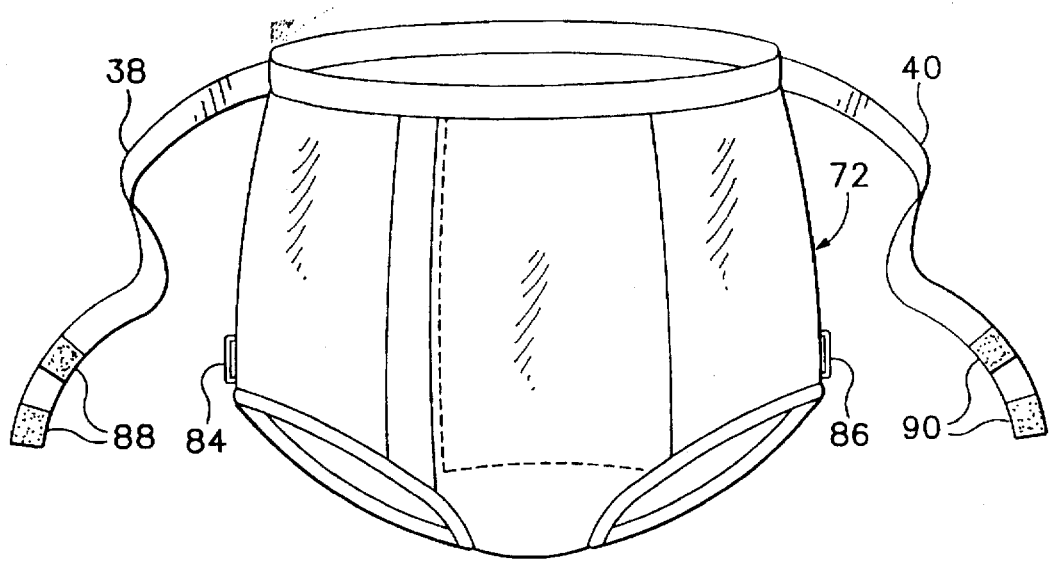
FIG. 9 is a front elevation of the undergarment of the invention bearing the fixing mechanism therefor.

Referring now to FIG. 4, straps 38, 40 are depicted, and pass through channels 30, entering and exiting channel 30 by means of slots 32, 34. Straps 38 and 40 and fixing-mechanism receivers 26, 28 comprise what is referred to herein as a fixing mechanism for holding flow-restricting device 10 in place. Flow-restricting device 10 and the fixing mechanism comprise what is referred to herein as a male incontinence treatment device.

Referring now to FIGS. 5 and 6, flow-restricting device 10 is depicted in an environmental view positioned adjacent the groin 42 of a wearer 44, (partially shown). Device 10 is depicted as compressing the urethra 46, which extends from the bladder 48 through the prostate gland 50. Urethra 46 passes through the penis, or penile shaft, 52 above the scrotum 54 and may be compressed between flow-restricting device 10 and the pubic bone, or pubic synthesis 56. As previously noted, the reason that the incontinence treatment device of the invention is needed is due to a malfunction of urethral sphincter 58, which may be damaged during the course of prostate surgery, typically by the severing of nerve connections to the muscle, or which may exist in a weakened condition as a result of other causes.

As seen, particularly in FIG. 6, post 18 is operable, along with urethra-bearing surface 20, to constrict the wearer's urethra 46 to its closed condition by compressing the urethra between urethra-bearing surface 20 and pubic bone 56. The concave form of penis-cradling surfaces 22, 24 allow post 18 to project into the surface of the penile shaft, placing urethra-bearing surface 20 into contact with the skin directly overlaying urethra 46, thereby compressing the urethra between post 18 and pubic synthesis 56. At the same time, the other penile structure are received in penis-cradling surfaces 22, 24 in a substantially non-compressed state. Such urethral constriction is accomplished without significantly diminishing blood flow through the corpus cavernosum 60, 62, and the corpus spongiosis 64. Neither does flow-restricting device 10 significantly restrict the penile veins, shown at 66, 68, or the bulbous corpus spongiosum 70. The blood-carrying portions in penile shaft 52 are substantially located in the penis-cradling surfaces 22, 24, so that they are not compressed. This feature provides for maintaining the urethra in a closed position without cutting off normal blood flow to the penis, thereby eliminating the possibility of tissue necrosis or artificially-induced erections.

Referring now to FIG. 7, an undergarment, or brief, is depicted generally at 72, and includes flow-restricting device 10 attached thereto by means of a fixing mechanism, depicted generally at 74. Brief 72 is of conventional design, and may or may not include a fly therein.

Brief 72 may include an absorbent pad 76, and an attachment mechanism therefor, which, in the preferred embodiment, takes the form of a pouch 78 which receives pad 76.

Straps 38 and 40 may be seen to be attached to a waistband 80 of brief 72 along the backside thereof, at an attachment point 82. Straps 38 and 40 then extend through their respective fixing mechanism receivers 26, 28, and through loops, or rings, 84, 86, which are located along the side panels of brief 72. Straps 38, 40 are held in place through loops 84, 86 by means of hook-and-loop fasteners, depicted at 88, 90, respectively. It should be appreciated that the fixing mechanism of the invention may include a pair of straps, or a single strap, which are/is worn under a conventional set of briefs, and which extends around the wearer's waist, through the fixing mechanism receivers of flow-restricting device 10, and which then extend about the wearer's buttocks.

During the course of wearing device 10, it should be appreciated that the device may shift as the wearer moves. To prevent, or minimize such shifting, flow restricting device 10 may also be held in its operable position by the provision of a pair of briefs which have a pocket therein sized to receive device 10. Device 10 may also be equipped with hook-and-loop fasteners which mate with a similar structure on a pair of briefs.

Thus, a male incontinence treatment device has been disclosed which effectively stops the flow of urine by compressing the wearer's urethra without significantly compressing the blood-carrying portions of the penile shaft and its use does not result in a restriction of the penile blood supply. The device is substantially invisible under clothing and does not require the unfastening of clamps prior to urination. The device is inexpensive to manufacture, is made of biologically inert material, is hygienically safe, and is easy to clean.

Although a preferred embodiment of the invention has been disclosed herein, it should be appreciated that further variations and modifications may be made thereto without departing from the scope of the invention as defined in the appended claims.

I claim:

1. A male incontinence treatment device for preventing the flow of urine through the urethra of a wearer, comprising:

a flow-restricting device for pressing the penis against the pubic bone of a wearer, whereby the urethra is compressed to a closed condition; said flow-restricting device including a central body portion, a post extending rearwardly therefrom for constricting the wearer's urethra to its closed condition, wherein said post has a concave urethra-bearing surface thereon; and a fixing mechanism for holding said flow-restricting device in place against the base of the penis.

2. The male incontinence treatment device of claim 1 wherein said central body portion includes a pair of laterally extending wings extending from either side thereof and extending rearwardly, relative to the wearer, for laterally stabilizing said flow-restricting device, said wings being constructed and arranged to contact the groin of the wearer.

3. The male incontinence treatment device of claim 2 which further includes a curved, penis-cradling surface located on either side of said post.

4. The male incontinence treatment device of claim 1 wherein said fixing mechanism includes a fixing-mechanism receiver on said central body portion and straps to secure the flow-restricting device to the wearer.

5. The male incontinence treatment device of claim 4 which further includes a brief having an absorbent pad therein and an attachment mechanism for said absorbent pad, and wherein said straps are at least partially fixed to said brief.

6. The male incontinence treatment device of claim 4 wherein said fixing mechanism receiver includes plural slots formed in said central body portion.

7. A male incontinence treatment device for preventing the flow of urine through the urethra of a wearer, in combination with an undergarment, comprising:

a flow-restricting device for pressing the penis against the anterior surface of the pubic synthesis of a wearer, whereby the urethra is compressed to a closed condition; and a fixing mechanism for holding said flow-restricting device in place against the base of the penis, said fixing mechanism including straps which are at least partially attached to the undergarment.

8. The male incontinence treatment device of claim 7 wherein said flow-restricting device includes a central body portion having a pair of laterally extending wings extending from either side thereof and extending rearwardly, relative to the wearer, for laterally stabilizing said flow-restricting device, said wings being constructed and arranged to contact the groin of the wearer, and further having a urethra-bearing surface extending rearwardly for constricting the wearer's urethra to its closed condition, and curved, penis-cradling surfaces on either side of said urethra-bearing surface for cradling the wearer's penis.

9. The male incontinence treatment device of claim 8 wherein said urethra-bearing surface is concave.

10. The male incontinence treatment device of claim 7 wherein said fixing mechanism includes a fixing-mechanism receiver on said central body portion.

11. The male incontinence treatment device of claim 7 wherein said fixing mechanism receiver includes plural slots formed in said central body portion.

12. The male incontinence treatment device of claim 7 wherein said undergarment has an absorbent pad therein and an attachment mechanism for said absorbent pad.

13. A male incontinence treatment device for preventing the flow of urine through the urethra of a wearer, comprising:

a flow-restricting device, formed of a biologically inert material, for pressing the penis against the pubic bone of a wearer, whereby the urethra is compressed to a closed condition, said flow-restricting device having a central body portion and a pair of laterally extending wings extending from either side of said body portion and extending rearwardly, relative to the wearer, for laterally stabilizing said flow-restricting device, said wings being constructed and arranged to contact the groin of the wearer, and further having a post, including a concave, urethra-bearing surface thereon, for constricting the wearer's urethra to its closed condition, said post extending rearwardly from said central body, and a curved, penis-cradling surface on either side of said post for cradling the wearer's penis; and a fixing mechanism for holding said flow-restricting device in place against the base of the penis.

14. The male incontinence treatment device of claim 13 wherein said fixing mechanism includes a fixing-mechanism receiver on said central body portion and straps to secure the flow-restricting device to the wearer.

15. The male incontinence treatment device of claim 13 which further includes a brief having an absorbent pad therein and an attachment mechanism for said absorbent pad, and wherein said straps are at least partially fixed to said brief.

16. The male incontinence treatment device of claim 13 wherein said fixing mechanism receiver includes plural slots formed in said central body portion.

* * * * *